US006433153B1

(12) United States Patent
Donoho et al.

(10) Patent No.: US 6,433,153 B1
(45) Date of Patent: Aug. 13, 2002

(54) HUMAN CALCIUM DEPENDENT PROTEASES AND POLYNUCLEOTIDES ENCODING THE SAME

(75) Inventors: Gregory Donoho; C. Alexander Turner, Jr., both of The Woodlands, TX (US); Michael C. Nehls, Stockdorf (DE); Glenn Friedrich, Houston, TX (US); Brian Zambrowicz; Arthur T. Sands, both of The Woodlands, TX (US)

(73) Assignee: Lexicon Genetics Incorporated, The Woodlands, TX (US)

( * ) Notice: Subject to any disclaimer, the term of this patent is extended or adjusted under 35 U.S.C. 154(b) by 0 days.

(21) Appl. No.: 09/653,839

(22) Filed: Sep. 1, 2000

Related U.S. Application Data
(60) Provisional application No. 60/152,057, filed on Sep. 2, 1999.

(51) Int. Cl.$^7$ .......................... C07H 21/04; C12N 9/50
(52) U.S. Cl. ........................ 536/23.2; 435/219
(58) Field of Search ...................... 536/23.2; 435/219

(56) References Cited

U.S. PATENT DOCUMENTS

| | | | |
|---|---|---|---|
| 4,215,051 | A | 7/1980 | Schroeder et al. |
| 4,376,110 | A | 3/1983 | David et al. |
| 4,946,778 | A | 8/1990 | Ladner et al. |
| 5,837,458 | A | 11/1998 | Minshull et al. |
| 5,869,336 | A | 2/1999 | Meyer et al. |
| 5,877,397 | A | 3/1999 | Lonberg et al. |
| 6,075,181 | A | 6/2000 | Kucherlapati et al. |

FOREIGN PATENT DOCUMENTS

| | | |
|---|---|---|
| EP | 1 059 353 A2 | 12/2000 |
| WO | WO 96/16175 | 5/1996 |
| WO | WO 00/58473 | 10/2000 |
| WO | WO 00 78933 A2 | 12/2000 |

OTHER PUBLICATIONS

Ohno et al. Evolutioanry origin of a calcium–dependent protease by fusion of genes for a thiol protease and a calcium–binding protein. Nature 312 (5994), 566–570 (1984).*
Dear et al, 1999, "CAPN11: A Calpain with High mRNA Levels in Testis and Located on Chromosome 6", Genomics 59:24.
Bird et al, 1988, "Single–Chain Antigen–Binding Proteins", Science 242:423–426.
Bitter et al, 1987, "Expression and Secretion Vectors for Yeast", Methods in Enzymology 153:516–544.
Colbere–Garapin et al, 1981, "A New Dominant Hybrid Selective Marker for Higher Eukaryotic Cells", J. Mol. Biol. 150:1–14.

Gautier et al, 1987, "α–anomeric and β–DNA IV;α–anomeric tetrathymidylates convalently linked to intercalating oxazolopyridocarbazole. Synthesis, physio–chemical properties and poly (rA) binding", Nucleic Acids Research 15(16):6625–6641.
Greenspan et al, 1993, "Idiotypes: structure and immuno–genicity", FASEB Journal 7:437–444.
Huse et al, 1989, "Generation of a Large Combinatorial Library of the Immunoglobulin Repertoire in Phage Lambda", Science 246:1275–1281.
Huston et al, 1988, "Protein engineering of antibody binding sites: Recovery of specific activity in an anti–digoxin sin–gle–chain Fv analogue produced in *Escherichia coli*", Proc. Natl. Acad. Sci. USA 85:5879–5883.
Inoue et al, 1987, "Sequence–dependent hydrolysis of RNA using modified olingonucleotide splints and R Nase H", FEBS Letters 215(2):327–330.
Inoue et al, 1987, "Synthesis and hybridization studies on two complementary nona(2'–O–methyl)ribonucleotides", Nucleic Acids Research 15(15):6131–6149.
Inouye & Inouye, 1985, "Up–promoter mutations in the lpp gene of *Escherichia coli*", Nucleic Acids Research 13(9):3101–3110.
Kohler & Milstein, 1975, "Continuous cultures of fused cells secreting antibody of predefined specificity", Nature 256:495–497.
Logan et al, 1984, "Adenovirus tripartite leader sequence enhances translation of mRNAs late after infection", Proc. Natl. Acad. Sci. USA 81:3655–3659.
Lowy et al, 1980, "Isolation of Transforming DNA: Cloning the Hamster aprt Gene", Cell 22:817–823.
Morrison et al, 1984, "Chimeric human antibody molecules: Mouse antigen–binding domains with human constant region domains", Proc. Natl. Acad. Sci. USA 81:6851–6855.
Mulligan & Berg, 1981, "Selection for animal cells that express the *Escherichia coli*gene coding for xanthine–gua–nine phosphoribosyltransferase", Proc. Natl. Acad. Sci. USA 78(4):2072–2076.
Neuberger et al, 1984, "Recombinant antibodies possessing novel effector functions", Nature 312:604–608.
Nisonoff, 1991, "Idiotypes: Concepts and Applications", J. of Immunology 147:2429–2438.
O'Hare et al, 1981, "Transformation of mouse fibroblasts to methotrexate resistance by a recombinant plasmid express–ing a prokaryotic dihydrofolate reductase", Proc. Natl. Acad. Sci. USA 78(3):1527–1531.
Ruther et al, 1983, "Easy identification of cDNA clones", EMBO Journal 2(10):1791–1794.
Santerre et al, 1984, "Expression of prokaryotic genes for hygromycin B and G418 resistance as dominant–selection markers in mouse L cells", Gene 30:147–156.

(List continued on next page.)

*Primary Examiner*—Ponnathapu Achutamurthy
*Assistant Examiner*—Yong Pak

(57) ABSTRACT

Novel human polynucleotide and polypeptide sequences are disclosed that can be used in therapeutic, diagnostic, and pharmacogenomic applications.

2 Claims, No Drawings

OTHER PUBLICATIONS

Sarin et al, 1988, "Inhibition of acquired immunodeficiency syndrome virus by oligodeoxynucleoxynucleoside methylphosphonates", Proc. Natl. Acad. Sci. USA 85:7448–7451.

Smith et al, 1983, "Molecular Engineering of the Autographa californica Nuclear Polyhedrosis Virus Genome: Deletion Mutations within the Polyhedrin Gene", J. Virol. 46(2):584–593.

Stein et al, 1988, "Physiochemical properties of phosphorothioate oligodeoxynucleotides", Nucleic Acids Research 16(8):3209–3221.

Szybalska & Szybalski, 1962, "Genetics of Human Cell Lines, IV. DNA–Mediated Heritable Transformation of a Biochemical Trait", Proc. Natl. Acad. Sci. USA 48:2026–2034.

Takeda et al, 1985, "Construction of chimaeric processed immunoglobulin genes containing mouse variable and human constant region sequences", Nature 314:452–454.

Van Heeke et al, 1989, "Expression of Human Asparagine Synthetase in *Escherichia coli*", J. Biol. Chemistry 264(10):5503–5510.

Ward et al, 1989, "Binding activities of a repertoire of single immunoglobulin variable domains secreted from *Escherichia coli*", Nature 341:544–546.

Wigler et al, 1977, "Transfer of Purified Herpes Virus Thymidine Kinase Gene to Cultured Mouse Cell", Cell 11:223–232.

Wigler et al, 1980, "Transformation of mammalian cells with an amplifiable dominant–acting gene", Proc. Natl. Acad. Sci. USA 77(6):3567–3570.

* cited by examiner

SEQUENCE LISTING

```
<160> NUMBER OF SEQ ID NOS: 9

<210> SEQ ID NO 1
<211> LENGTH: 2220
<212> TYPE: DNA
<213> ORGANISM: homo sapiens

<400> SEQUENCE: 1
atgctgtact ccccagggcc gagtcttccg gagtcagcag agagcctgga tggatcacag      60
gaggataagc ctcggggctc atgtgcggag cccactttta ctgatacggg aatggtggct     120
cacataaaca acagccggct caaggccaag ggcgtgggcc agcacgacaa cgcccagaac     180
tttggtaacc agagctttga ggagctgcga gcagcctgtc taagaaaggg ggagctcttc     240
gaggacccct tattccctgc tgaacccagc tcactgggct tcaaggacct gggccccaac     300
tccaaaaatg tgcagaacat ctcctggcag cggcccaagg atatcataaa caaccctcta     360
ttcatcatgg atgggatttc tccaacagac atctgccagg ggatcctcgg ggactgctgg     420
ctgctggctg ccatcggctc ccttaccacc tgccccaaac tgctataccg cgtggtgccc     480
agaggacaga gcttcaagaa aaactatgct ggcatcttcc attttcagat ttggcagttt     540
ggacagtggg tgaacgtggt ggtagatgac cggctgccca caaagaatga caagctggtg     600
tttgtgcact caaccgaacg cagtgagttc tggagtgccc tgctggagaa ggcgtatgcc     660
aagctgagtg ggtcctatga agcattgtca gggggcagta ccatggaggg ccttgaggac     720
ttcacaggag gcgtggccca gagcttccaa ctccagaggc cccctcagaa cctgctcagg     780
ctccttagga aggccgtgga gcgatcctcc ctcatgggtt gctccattga agtcaccagt     840
gatagtgaac tggaatccat gactgacaag atgctggtga gagggcacgc ttactctgtg     900
actggccttc aggatgtcca ctacagaggc aaaatggaaa cactgattcg ggtccggaat     960
ccctggggcc ggattgagtg gaatggagct tggagtgaca gtgccaggga gtgggaagag    1020
gtggcctcag acatccagat gcagctgctg cacaagacgg aggacgggga gttctggatg    1080
tcctaccaag atttcctgaa caacttcacg ctcctggaga tctgcaacct cacgcctgat    1140
acactctctg gggactacaa gagctactgg cacaccacct tctacgaggg cagctggcgc    1200
agaggcagct ccgcaggggg ctgcaggaac caccctggca cgttctggac caacccccag    1260
tttaagatct ctcttcctga gggggatgac ccagaggatg acgcagaggg caatgttgtg    1320
gtctgcacct gcctggtggc cctaatgcag aagaactggc ggcatgcacg gcagcaggga    1380
gcccagctgc agaccattgg ctttgtcctc tacgcggtcc caaaagagtt tcagaacatt    1440
caggatgtcc acttgaagaa ggaattcttc acgaagtatc aggaccacgg cttctcagag    1500
atcttcacca actcacggga ggtgagcagc caactccggc tgcctccggg ggaatatatc    1560
attattccct ccacctttga gccacacaga gatgctgact tcctgcttcg ggtcttcacc    1620
gagaagcaca gcgagtcatg ggaattggat gaagtcaact atgctgagca actccaagag    1680
```

-continued

```
gaaaaggtct ctgaggatga catggaccag gacttcctac atttgtttaa gatagtggca    1740
ggagagggca aggagatagg ggtgtatgag ctccagaggc tgctcaacag gatggccatc    1800
aaattcaaaa gcttcaagac caagggcttt ggcctggatg cttgccgctg catgatcaac    1860
ctcatggata agatggctc tggcaagctg ggcttctag agttcaagat cctgtggaaa     1920
aaactcaaga aatggatgga catcttcaga gagtgtgacc aggaccattc aggcaccttg    1980
aactcctatg agatgcgcct ggttattgag aaagcaggca tcaagctgaa caacaaggta    2040
atgcaggtcc tggtggccag gtatgcagat gatgacctga tcatagactt tgacagcttc    2100
atcagctgtt tcctgaggct aaagaccatg ttcacattct ttctaaccat ggaccccaag    2160
aatactggcc atatttgctt gagcctggaa cagtggctgc agatgaccat gtggggatag    2220
```

<210> SEQ ID NO 2
<211> LENGTH: 739
<212> TYPE: PRT
<213> ORGANISM: homo sapiens

<400> SEQUENCE: 2

```
Met Leu Tyr Ser Pro Gly Pro Ser Leu Pro Glu Ser Ala Glu Ser Leu
  1               5                  10                  15

Asp Gly Ser Gln Glu Asp Lys Pro Arg Gly Ser Cys Ala Glu Pro Thr
             20                  25                  30

Phe Thr Asp Thr Gly Met Val Ala His Ile Asn Asn Ser Arg Leu Lys
         35                  40                  45

Ala Lys Gly Val Gly Gln His Asp Asn Ala Gln Asn Phe Gly Asn Gln
     50                  55                  60

Ser Phe Glu Glu Leu Arg Ala Ala Cys Leu Arg Lys Gly Glu Leu Phe
 65                  70                  75                  80

Glu Asp Pro Leu Phe Pro Ala Glu Pro Ser Ser Leu Gly Phe Lys Asp
                 85                  90                  95

Leu Gly Pro Asn Ser Lys Asn Val Gln Asn Ile Ser Trp Gln Arg Pro
            100                 105                 110

Lys Asp Ile Ile Asn Asn Pro Leu Phe Ile Met Asp Gly Ile Ser Pro
        115                 120                 125

Thr Asp Ile Cys Gln Gly Ile Leu Gly Asp Cys Trp Leu Leu Ala Ala
    130                 135                 140

Ile Gly Ser Leu Thr Thr Cys Pro Lys Leu Leu Tyr Arg Val Val Pro
145                 150                 155                 160

Arg Gly Gln Ser Phe Lys Lys Asn Tyr Ala Gly Ile Phe His Phe Gln
                165                 170                 175

Ile Trp Gln Phe Gly Gln Trp Val Asn Val Val Asp Asp Arg Leu
            180                 185                 190

Pro Thr Lys Asn Asp Lys Leu Val Phe Val His Ser Thr Glu Arg Ser
        195                 200                 205

Glu Phe Trp Ser Ala Leu Leu Glu Lys Ala Tyr Ala Lys Leu Ser Gly
    210                 215                 220

Ser Tyr Glu Ala Leu Ser Gly Gly Ser Thr Met Glu Gly Leu Glu Asp
225                 230                 235                 240

Phe Thr Gly Gly Val Ala Gln Ser Phe Gln Leu Gln Arg Pro Pro Gln
                245                 250                 255

Asn Leu Leu Arg Leu Leu Arg Lys Ala Val Glu Arg Ser Ser Leu Met
            260                 265                 270

Gly Cys Ser Ile Glu Val Thr Ser Asp Ser Glu Leu Glu Ser Met Thr
```

-continued

```
                275                 280                 285
Asp Lys Met Leu Val Arg Gly His Ala Tyr Ser Val Thr Gly Leu Gln
                290                 295                 300
Asp Val His Tyr Arg Gly Lys Met Glu Thr Leu Ile Arg Val Arg Asn
305                 310                 315                 320
Pro Trp Gly Arg Ile Glu Trp Asn Gly Ala Trp Ser Asp Ser Ala Arg
                325                 330                 335
Glu Trp Glu Glu Val Ala Ser Asp Ile Gln Met Gln Leu Leu His Lys
                340                 345                 350
Thr Glu Asp Gly Glu Phe Trp Met Ser Tyr Gln Asp Phe Leu Asn Asn
                355                 360                 365
Phe Thr Leu Leu Glu Ile Cys Asn Leu Thr Pro Asp Thr Leu Ser Gly
                370                 375                 380
Asp Tyr Lys Ser Tyr Trp His Thr Thr Phe Tyr Glu Gly Ser Trp Arg
385                 390                 395                 400
Arg Gly Ser Ser Ala Gly Gly Cys Arg Asn His Pro Gly Thr Phe Trp
                405                 410                 415
Thr Asn Pro Gln Phe Lys Ile Ser Leu Pro Glu Gly Asp Asp Pro Glu
                420                 425                 430
Asp Asp Ala Glu Gly Asn Val Val Cys Thr Cys Leu Val Ala Leu
                435                 440                 445
Met Gln Lys Asn Trp Arg His Ala Arg Gln Gln Gly Ala Gln Leu Gln
450                 455                 460
Thr Ile Gly Phe Val Leu Tyr Ala Val Pro Lys Glu Phe Gln Asn Ile
465                 470                 475                 480
Gln Asp Val His Leu Lys Lys Glu Phe Phe Thr Lys Tyr Gln Asp His
                485                 490                 495
Gly Phe Ser Glu Ile Phe Thr Asn Ser Arg Glu Val Ser Ser Gln Leu
                500                 505                 510
Arg Leu Pro Pro Gly Glu Tyr Ile Ile Ile Pro Ser Thr Phe Glu Pro
                515                 520                 525
His Arg Asp Ala Asp Phe Leu Leu Arg Val Phe Thr Glu Lys His Ser
                530                 535                 540
Glu Ser Trp Glu Leu Asp Glu Val Asn Tyr Ala Glu Gln Leu Gln Glu
545                 550                 555                 560
Glu Lys Val Ser Glu Asp Asp Met Asp Gln Asp Phe Leu His Leu Phe
                565                 570                 575
Lys Ile Val Ala Gly Glu Gly Lys Glu Ile Gly Val Tyr Glu Leu Gln
                580                 585                 590
Arg Leu Leu Asn Arg Met Ala Ile Lys Phe Lys Ser Phe Lys Thr Lys
                595                 600                 605
Gly Phe Gly Leu Asp Ala Cys Arg Cys Met Ile Asn Leu Met Asp Lys
                610                 615                 620
Asp Gly Ser Gly Lys Leu Gly Leu Leu Glu Phe Lys Ile Leu Trp Lys
625                 630                 635                 640
Lys Leu Lys Lys Trp Met Asp Ile Phe Arg Glu Cys Asp Gln Asp His
                645                 650                 655
Ser Gly Thr Leu Asn Ser Tyr Glu Met Arg Leu Val Ile Glu Lys Ala
                660                 665                 670
Gly Ile Lys Leu Asn Asn Lys Val Met Gln Val Leu Val Ala Arg Tyr
                675                 680                 685
Ala Asp Asp Asp Leu Ile Ile Asp Phe Asp Ser Phe Ile Ser Cys Phe
690                 695                 700
```

| | | | | | | | | | | | | | | |
|---|---|---|---|---|---|---|---|---|---|---|---|---|---|---|
|Leu|Arg|Leu|Lys|Thr|Met|Phe|Thr|Phe|Phe|Leu|Thr|Met|Asp|Pro|Lys|
|705| | | | |710| | | |715| | | | |720|

| | | | | | | | | | | | | |
|---|---|---|---|---|---|---|---|---|---|---|---|---|
|Asn|Thr|Gly|His|Ile|Cys|Leu|Ser|Leu|Glu|Gln|Trp|Leu|Gln|Met|Thr|
| | | | |725| | | | |730| | | | |735|

Met Trp Gly

<210> SEQ ID NO 3
<211> LENGTH: 2172
<212> TYPE: DNA
<213> ORGANISM: homo sapiens

<400> SEQUENCE: 3

| | | | | | |
|---|---|---|---|---|---|
|atgctgtact|ccccagggcc|gagtcttccg|gagtcagcag|agagcctgga|tggatcacag|60|
|gaggataagc|ctcggggctc|atgtgcggag|cccactttta|ctgatacggg|aatggtggct|120|
|cacataaaca|acagccggct|caaggccaag|gcgtgggcc|agcacgacaa|cgcccagaac|180|
|tttggtaacc|agagctttga|ggagctgcga|gcagcctgtc|taagaaaggg|ggagctcttc|240|
|gaggacccct|tattccctgc|tgaacccagc|tcactgggct|tcaaggacct|gggccccaac|300|
|tccaaaaatg|tgcagaacat|tcctggcag|cggcccaagg|atatcataaa|caaccctcta|360|
|ttcatcatgg|atgggatttc|tccaacagac|atctgccagg|ggatcctcgg|ggactgctgg|420|
|ctgctggctg|ccatcggctc|ccttaccacc|tgccccaaac|tgctataccg|cgtggtgccc|480|
|agaggacaga|gcttcaagaa|aaactatgct|ggcatcttcc|attttcagat|ttggcagttt|540|
|ggacagtggg|tgaacgtggt|ggtagatgac|cggctgccca|caaagaatga|caagctggtg|600|
|tttgtgcact|caaccgaacg|cagtgagttc|tggagtgccc|tgctggagaa|ggcgtatgcc|660|
|aagctgagtg|ggtcctatga|agcattgtca|gggggcagta|ccatggaggg|ccttgaggac|720|
|ttcacaggag|gcgtggccca|gagcttccaa|ctccagaggc|cccctcagaa|cctgctcagg|780|
|ctccttagga|aggccgtgga|gcgatcctcc|ctcatggggtt|gctccattga|agtcaccagt|840|
|gatagtgaac|tggaatccat|gactgacaag|atgctggtga|gagggcacgc|ttactctgtg|900|
|actggccttc|aggatgtcca|ctacagaggc|aaaatggaaa|cactgattcg|ggtccggaat|960|
|ccctggggcc|ggattgagtg|gaatggagct|tggagtgaca|gtgccaggga|gtgggaagag|1020|
|gtggcctcag|acatccagat|gcagctgctg|cacaagacgg|aggacgggga|gttctggatg|1080|
|tcctaccaag|atttcctgaa|caacttcacg|ctcctggaga|tctgcaacct|cacgcctgat|1140|
|acactctctg|gggactacaa|gagctactgg|cacaccacct|tctacgaggg|cagctggcgc|1200|
|agaggcagct|ccgcagggg|ctgcaggaac|caccctggca|cgttctggac|caaccccag|1260|
|tttaagatct|ctcttcctga|ggggatgac|ccagaggatg|acgcagaggg|caatgttgtg|1320|
|gtctgcacct|gcctggtggc|cctaatgcag|aagaactggc|ggcatgcacg|gcagcaggga|1380|
|gcccagctgc|agaccattgg|ctttgtcctc|tacgcggtcc|caaagagtt|tcagaacatt|1440|
|caggatgtcc|acttgaagaa|ggaattcttc|acgaagtatc|aggaccacgg|cttctcagag|1500|
|atcttcacca|actcacggga|ggtgagcagc|caactccgc|tgcctccggg|ggaatatatc|1560|
|attattccct|ccaccttga|gccacacaga|gatgctgact|tcctgcttcg|ggtcttcacc|1620|
|gagaagcaca|gcgagtcatg|ggaattggat|gaagtcaact|atgctgagca|actccaagag|1680|
|gaaaaggtct|ctgaggatga|catggaccag|gacttcctac|atttgtttaa|gatagtggca|1740|
|ggagagggca|aggagatagg|ggtgtatgag|ctccagaggc|tgctcaacag|gatggccatc|1800|
|aaattcaaaa|gcttcaagac|caagggctttt|ggcctggatg|cttgccgctg|catgatcaac|1860|

-continued

```
ctcatggata aagatggctc tggcaagctg gggcttctag agttcaagat cctgtggaaa   1920
aaactcaaga aatggatgga catcttcaga gagtgtgacc aggaccattc aggcaccttg   1980
aactcctatg agatgcgcct ggttattgag aaagcaggca tcaagctgaa caacaaggta   2040
atgcaggtcc tggtggccag gtatgcagat gatgacctga tcatagactt tgacagcttc   2100
atcagctgtt tcctgaggct aaagaccatg ttcatggctg cagatgacca tgtggggata   2160
gaggcgctgt ag                                                       2172
```

<210> SEQ ID NO 4
<211> LENGTH: 723
<212> TYPE: PRT
<213> ORGANISM: homo sapiens

<400> SEQUENCE: 4

| | | | | | | | | | | | | | | |
|---|---|---|---|---|---|---|---|---|---|---|---|---|---|---|
| Met | Leu | Tyr | Ser | Pro | Gly | Pro | Ser | Leu | Pro | Glu | Ser | Ala | Glu | Ser | Leu |
| 1 | | | | 5 | | | | | 10 | | | | | 15 | |
| Asp | Gly | Ser | Gln | Glu | Asp | Lys | Pro | Arg | Gly | Ser | Cys | Ala | Glu | Pro | Thr |
| | | | 20 | | | | | 25 | | | | | 30 | | |
| Phe | Thr | Asp | Thr | Gly | Met | Val | Ala | His | Ile | Asn | Asn | Ser | Arg | Leu | Lys |
| | | 35 | | | | | 40 | | | | | 45 | | | |
| Ala | Lys | Gly | Val | Gly | Gln | His | Asp | Asn | Ala | Gln | Asn | Phe | Gly | Asn | Gln |
| | 50 | | | | | 55 | | | | | 60 | | | | |
| Ser | Phe | Glu | Glu | Leu | Arg | Ala | Ala | Cys | Leu | Arg | Lys | Gly | Glu | Leu | Phe |
| 65 | | | | | 70 | | | | | 75 | | | | | 80 |
| Glu | Asp | Pro | Leu | Phe | Pro | Ala | Glu | Pro | Ser | Ser | Leu | Gly | Phe | Lys | Asp |
| | | | | 85 | | | | | 90 | | | | | 95 | |
| Leu | Gly | Pro | Asn | Ser | Lys | Asn | Val | Gln | Asn | Ile | Ser | Trp | Gln | Arg | Pro |
| | | | 100 | | | | | 105 | | | | | 110 | | |
| Lys | Asp | Ile | Ile | Asn | Asn | Pro | Leu | Phe | Ile | Met | Asp | Gly | Ile | Ser | Pro |
| | | 115 | | | | | 120 | | | | | 125 | | | |
| Thr | Asp | Ile | Cys | Gln | Gly | Ile | Leu | Gly | Asp | Cys | Trp | Leu | Leu | Ala | Ala |
| | 130 | | | | | 135 | | | | | 140 | | | | |
| Ile | Gly | Ser | Leu | Thr | Thr | Cys | Pro | Lys | Leu | Leu | Tyr | Arg | Val | Val | Pro |
| 145 | | | | | 150 | | | | | 155 | | | | | 160 |
| Arg | Gly | Gln | Ser | Phe | Lys | Lys | Asn | Tyr | Ala | Gly | Ile | Phe | His | Phe | Gln |
| | | | | 165 | | | | | 170 | | | | | 175 | |
| Ile | Trp | Gln | Phe | Gly | Gln | Trp | Val | Asn | Val | Val | Asp | Asp | Arg | Leu |
| | | | 180 | | | | | 185 | | | | | 190 | | |
| Pro | Thr | Lys | Asn | Asp | Lys | Leu | Val | Phe | Val | His | Ser | Thr | Glu | Arg | Ser |
| | | 195 | | | | | 200 | | | | | 205 | | | |
| Glu | Phe | Trp | Ser | Ala | Leu | Leu | Glu | Lys | Ala | Tyr | Ala | Lys | Leu | Ser | Gly |
| | 210 | | | | | 215 | | | | | 220 | | | | |
| Ser | Tyr | Glu | Ala | Leu | Ser | Gly | Gly | Ser | Thr | Met | Glu | Gly | Leu | Glu | Asp |
| 225 | | | | | 230 | | | | | 235 | | | | | 240 |
| Phe | Thr | Gly | Gly | Val | Ala | Gln | Ser | Phe | Gln | Leu | Gln | Arg | Pro | Pro | Gln |
| | | | | 245 | | | | | 250 | | | | | 255 | |
| Asn | Leu | Leu | Arg | Leu | Leu | Arg | Lys | Ala | Val | Glu | Arg | Ser | Ser | Leu | Met |
| | | | 260 | | | | | 265 | | | | | 270 | | |
| Gly | Cys | Ser | Ile | Glu | Val | Thr | Ser | Asp | Ser | Glu | Leu | Glu | Ser | Met | Thr |
| | | 275 | | | | | 280 | | | | | 285 | | | |
| Asp | Lys | Met | Leu | Val | Arg | Gly | His | Ala | Tyr | Ser | Val | Thr | Gly | Leu | Gln |
| | 290 | | | | | 295 | | | | | 300 | | | | |
| Asp | Val | His | Tyr | Arg | Gly | Lys | Met | Glu | Thr | Leu | Ile | Arg | Val | Arg | Asn |
| 305 | | | | | 310 | | | | | 315 | | | | | 320 |

-continued

```
Pro Trp Gly Arg Ile Glu Trp Asn Gly Ala Trp Ser Asp Ser Ala Arg
            325                 330                 335
Glu Trp Glu Glu Val Ala Ser Asp Ile Gln Met Gln Leu Leu His Lys
            340                 345                 350
Thr Glu Asp Gly Glu Phe Trp Met Ser Tyr Gln Asp Phe Leu Asn Asn
            355                 360                 365
Phe Thr Leu Leu Glu Ile Cys Asn Leu Thr Pro Asp Thr Leu Ser Gly
            370                 375                 380
Asp Tyr Lys Ser Tyr Trp His Thr Thr Phe Tyr Glu Gly Ser Trp Arg
385                 390                 395                 400
Arg Gly Ser Ser Ala Gly Gly Cys Arg Asn His Pro Gly Thr Phe Trp
            405                 410                 415
Thr Asn Pro Gln Phe Lys Ile Ser Leu Pro Glu Gly Asp Asp Pro Glu
            420                 425                 430
Asp Asp Ala Glu Gly Asn Val Val Cys Thr Cys Leu Val Ala Leu
            435                 440                 445
Met Gln Lys Asn Trp Arg His Ala Arg Gln Gln Gly Ala Gln Leu Gln
            450                 455                 460
Thr Ile Gly Phe Val Leu Tyr Ala Val Pro Lys Glu Phe Gln Asn Ile
465                 470                 475                 480
Gln Asp Val His Leu Lys Lys Glu Phe Phe Thr Lys Tyr Gln Asp His
            485                 490                 495
Gly Phe Ser Glu Ile Phe Thr Asn Ser Arg Glu Val Ser Ser Gln Leu
            500                 505                 510
Arg Leu Pro Pro Gly Glu Tyr Ile Ile Ile Pro Ser Thr Phe Glu Pro
            515                 520                 525
His Arg Asp Ala Asp Phe Leu Leu Arg Val Phe Thr Glu Lys His Ser
            530                 535                 540
Glu Ser Trp Glu Leu Asp Glu Val Asn Tyr Ala Glu Gln Leu Gln Glu
545                 550                 555                 560
Glu Lys Val Ser Glu Asp Asp Met Asp Gln Asp Phe Leu His Leu Phe
            565                 570                 575
Lys Ile Val Ala Gly Glu Gly Lys Glu Ile Gly Val Tyr Glu Leu Gln
            580                 585                 590
Arg Leu Leu Asn Arg Met Ala Ile Lys Phe Lys Ser Phe Lys Thr Lys
            595                 600                 605
Gly Phe Gly Leu Asp Ala Cys Arg Cys Met Ile Asn Leu Met Asp Lys
            610                 615                 620
Asp Gly Ser Gly Lys Leu Gly Leu Leu Glu Phe Lys Ile Leu Trp Lys
625                 630                 635                 640
Lys Leu Lys Lys Trp Met Asp Ile Phe Arg Glu Cys Asp Gln Asp His
            645                 650                 655
Ser Gly Thr Leu Asn Ser Tyr Glu Met Arg Leu Val Ile Glu Lys Ala
            660                 665                 670
Gly Ile Lys Leu Asn Asn Lys Val Met Gln Val Leu Val Ala Arg Tyr
            675                 680                 685
Ala Asp Asp Asp Leu Ile Ile Asp Phe Asp Ser Phe Ile Ser Cys Phe
            690                 695                 700
Leu Arg Leu Lys Thr Met Phe Met Ala Ala Asp Asp His Val Gly Ile
705                 710                 715                 720
Glu Ala Leu
```

-continued

<210> SEQ ID NO 5
<211> LENGTH: 2109
<212> TYPE: DNA
<213> ORGANISM: homo sapiens

<400> SEQUENCE: 5

| | | | | | |
|---|---|---|---|---|---|
| atggtggctc | acataaacaa | cagccggctc | aaggccaagg | gcgtgggcca | gcacgacaac | 60 |
| gcccagaact | ttggtaacca | gagctttgag | agctgcgag | cagcctgtct | aagaaagggg | 120 |
| gagctcttcg | aggacccctt | attccctgct | gaacccagct | cactgggctt | caaggacctg | 180 |
| ggccccaact | ccaaaaatgt | gcagaacatc | tcctggcagg | gcccaagga | tatcataaac | 240 |
| aaccctctat | tcatcatgga | tgggatttct | ccaacagaca | tctgccaggg | gatcctcggg | 300 |
| gactgctggc | tgctggctgc | catcggctcc | cttaccacct | gccccaaact | gctataccgc | 360 |
| gtggtgccca | gaggacagag | cttcaagaaa | aactatgctg | gcatcttcca | ttttcagatt | 420 |
| tggcagtttg | gacagtgggt | gaacgtggtg | gtagatgacc | ggctgcccac | aaagaatgac | 480 |
| aagctggtgt | tgtgcactc | aaccgaacgc | agtgagttct | ggagtgccct | gctggagaag | 540 |
| gcgtatgcca | agctgagtgg | gtcctatgaa | gcattgtcag | ggggcagtac | catggagggc | 600 |
| cttgaggact | tcacaggagg | cgtggcccag | agcttccaac | tccagaggcc | ccctcagaac | 660 |
| ctgctcaggc | tccttaggaa | ggccgtggag | cgatcctccc | tcatggggttg | ctccattgaa | 720 |
| gtcaccagtg | atagtgaact | ggaatccatg | actgacaaga | tgctggtgag | agggcacgct | 780 |
| tactctgtga | ctggccttca | ggatgtccac | tacagaggca | aaatgaaac | actgattcgg | 840 |
| gtccggaatc | cctggggccg | gattgagtgg | aatggagctt | ggagtgacag | tgccagggag | 900 |
| tgggaagagg | tggcctcaga | catccagatg | cagctgctgc | acaagacgga | ggacggggag | 960 |
| ttctggatgt | cctaccaaga | tttcctgaac | aacttcacgc | tcctggagat | ctgcaaccctc | 1020 |
| acgcctgata | cactctctgg | ggactacaag | agctactggc | acaccacctt | ctacgagggc | 1080 |
| agctggcgca | gaggcagctc | cgcaggggc | tgcaggaacc | accctggcac | gttctggacc | 1140 |
| aaccccagt | ttaagatctc | tcttcctgag | ggggatgacc | cagaggatga | cgcagagggc | 1200 |
| aatgttgtgg | tctgcacctg | cctggtggcc | ctaatgcaga | agaactggcg | gcatgcacgg | 1260 |
| cagcagggag | cccagctgca | gaccattggc | tttgtcctct | acgcggtccc | aaaagagttt | 1320 |
| cagaacattc | aggatgtcca | cttgaagaag | gaattcttca | cgaagtatca | ggaccacggc | 1380 |
| ttctcagaga | tcttcaccaa | ctcacggag | gtgagcagcc | aactccggct | gcctccgggg | 1440 |
| gaatatatca | ttattccctc | caccttttgag | ccacacagag | atgctgactt | cctgcttcgg | 1500 |
| gtcttcaccg | agaagcacag | cgagtcatgg | gaattggatg | aagtcaacta | tgctgagcaa | 1560 |
| ctccaagagg | aaaaggtctc | tgaggatgac | atggaccagg | acttcctaca | tttgtttaag | 1620 |
| atagtggcag | gagagggcaa | ggagataggg | gtgtatgagc | tccagaggct | gctcaacagg | 1680 |
| atggccatca | aattcaaaag | cttcaagacc | aagggctttg | gcctggatgc | ttccgctgc | 1740 |
| atgatcaacc | tcatggataa | agatggctct | ggcaagctgg | ggcttctaga | gttcaagatc | 1800 |
| ctgtggaaaa | aactcaagaa | atggatggac | atcttcagag | agtgtgacca | ggaccattca | 1860 |
| ggcaccttga | actcctatga | tgatcgcctg | gttattgaga | aagcaggcat | caagctgaac | 1920 |
| aacaaggtaa | tgcaggtcct | ggtggccagg | tatgcagatg | atgacctgat | catagacttt | 1980 |
| gacagcttca | tcagctgttt | cctgaggcta | aagaccatgt | tcacattctt | tctaaccatg | 2040 |
| gaccccaaga | atactggcca | tatttgcttg | agcctggaac | agtggctgca | gatgaccatg | 2100 |
| tggggatag | | | | | | 2109 |

```
<210> SEQ ID NO 6
<211> LENGTH: 702
<212> TYPE: PRT
<213> ORGANISM: homo sapiens

<400> SEQUENCE: 6

Met Val Ala His Ile Asn Asn Ser Arg Leu Lys Ala Lys Gly Val Gly
  1               5                  10                  15

Gln His Asp Asn Ala Gln Asn Phe Gly Asn Gln Ser Phe Glu Glu Leu
                 20                  25                  30

Arg Ala Ala Cys Leu Arg Lys Gly Glu Leu Phe Glu Asp Pro Leu Phe
             35                  40                  45

Pro Ala Glu Pro Ser Ser Leu Gly Phe Lys Asp Leu Gly Pro Asn Ser
         50                  55                  60

Lys Asn Val Gln Asn Ile Ser Trp Gln Arg Pro Lys Asp Ile Ile Asn
 65                  70                  75                  80

Asn Pro Leu Phe Ile Met Asp Gly Ile Ser Pro Thr Asp Ile Cys Gln
                 85                  90                  95

Gly Ile Leu Gly Asp Cys Trp Leu Leu Ala Ala Ile Gly Ser Leu Thr
            100                 105                 110

Thr Cys Pro Lys Leu Leu Tyr Arg Val Val Pro Arg Gly Gln Ser Phe
            115                 120                 125

Lys Lys Asn Tyr Ala Gly Ile Phe His Phe Gln Ile Trp Gln Phe Gly
130                 135                 140

Gln Trp Val Asn Val Val Asp Asp Arg Leu Pro Thr Lys Asn Asp
145                 150                 155                 160

Lys Leu Val Phe Val His Ser Thr Glu Arg Ser Glu Phe Trp Ser Ala
                165                 170                 175

Leu Leu Glu Lys Ala Tyr Ala Lys Leu Ser Gly Ser Tyr Glu Ala Leu
            180                 185                 190

Ser Gly Gly Ser Thr Met Glu Gly Leu Glu Asp Phe Thr Gly Gly Val
        195                 200                 205

Ala Gln Ser Phe Gln Leu Gln Arg Pro Pro Gln Asn Leu Leu Arg Leu
    210                 215                 220

Leu Arg Lys Ala Val Glu Arg Ser Ser Leu Met Gly Cys Ser Ile Glu
225                 230                 235                 240

Val Thr Ser Asp Ser Glu Leu Glu Ser Met Thr Asp Lys Met Leu Val
                245                 250                 255

Arg Gly His Ala Tyr Ser Val Thr Gly Leu Gln Asp Val His Tyr Arg
            260                 265                 270

Gly Lys Met Glu Thr Leu Ile Arg Val Arg Asn Pro Trp Gly Arg Ile
        275                 280                 285

Glu Trp Asn Gly Ala Trp Ser Asp Ser Ala Arg Glu Trp Glu Glu Val
    290                 295                 300

Ala Ser Asp Ile Gln Met Gln Leu Leu His Lys Thr Glu Asp Gly Glu
305                 310                 315                 320

Phe Trp Met Ser Tyr Gln Asp Phe Leu Asn Asn Phe Thr Leu Leu Glu
                325                 330                 335

Ile Cys Asn Leu Thr Pro Asp Thr Leu Ser Gly Asp Tyr Lys Ser Tyr
            340                 345                 350

Trp His Thr Thr Phe Tyr Glu Gly Ser Trp Arg Arg Gly Ser Ser Ala
        355                 360                 365

Gly Gly Cys Arg Asn His Pro Gly Thr Phe Trp Thr Asn Pro Gln Phe
    370                 375                 380
```

```
Lys Ile Ser Leu Pro Glu Gly Asp Asp Pro Glu Asp Ala Glu Gly
385                 390                 395                 400

Asn Val Val Cys Thr Cys Leu Val Ala Leu Met Gln Lys Asn Trp
            405                 410                 415

Arg His Ala Arg Gln Gln Gly Ala Gln Leu Gln Thr Ile Gly Phe Val
            420                 425                 430

Leu Tyr Ala Val Pro Lys Glu Phe Gln Asn Ile Gln Asp Val His Leu
            435                 440                 445

Lys Lys Glu Phe Phe Thr Lys Tyr Gln Asp His Gly Phe Ser Glu Ile
450                 455                 460

Phe Thr Asn Ser Arg Glu Val Ser Ser Gln Leu Arg Leu Pro Pro Gly
465                 470                 475                 480

Glu Tyr Ile Ile Ile Pro Ser Thr Phe Glu Pro His Arg Asp Ala Asp
                485                 490                 495

Phe Leu Leu Arg Val Phe Thr Glu Lys His Ser Glu Ser Trp Glu Leu
            500                 505                 510

Asp Glu Val Asn Tyr Ala Glu Gln Leu Gln Glu Glu Lys Val Ser Glu
            515                 520                 525

Asp Asp Met Asp Gln Asp Phe Leu His Leu Phe Lys Ile Val Ala Gly
530                 535                 540

Glu Gly Lys Glu Ile Gly Val Tyr Glu Leu Gln Arg Leu Leu Asn Arg
545                 550                 555                 560

Met Ala Ile Lys Phe Lys Ser Phe Lys Thr Lys Gly Phe Gly Leu Asp
                565                 570                 575

Ala Cys Arg Cys Met Ile Asn Leu Met Asp Lys Asp Gly Ser Gly Lys
            580                 585                 590

Leu Gly Leu Leu Glu Phe Lys Ile Leu Trp Lys Lys Leu Lys Lys Trp
595                 600                 605

Met Asp Ile Phe Arg Glu Cys Asp Gln Asp His Ser Gly Thr Leu Asn
            610                 615                 620

Ser Tyr Glu Met Arg Leu Val Ile Glu Lys Ala Gly Ile Lys Leu Asn
625                 630                 635                 640

Asn Lys Val Met Gln Val Leu Val Ala Arg Tyr Ala Asp Asp Asp Leu
                645                 650                 655

Ile Ile Asp Phe Asp Ser Phe Ile Ser Cys Phe Leu Arg Leu Lys Thr
            660                 665                 670

Met Phe Thr Phe Phe Leu Thr Met Asp Pro Lys Asn Thr Gly His Ile
            675                 680                 685

Cys Leu Ser Leu Glu Gln Trp Leu Gln Met Thr Met Trp Gly
    690                 695                 700

<210> SEQ ID NO 7
<211> LENGTH: 2061
<212> TYPE: DNA
<213> ORGANISM: homo sapiens

<400> SEQUENCE: 7
atggtggctc acataaacaa cagccggctc aaggccaagg gcgtgggcca gcacgacaac    60
gcccagaact ttgtaacca  gagctttgag gagctgcgag cagcctgtct aagaaagggg   120
gagctcttcg aggacccctt attccctgct gaacccagct cactgggctt caaggacctg   180
ggccccaact ccaaaaatgt gcagaacatc tcctggcagc ggcccaagga tatcataaac   240
aaccctctat tcatcatgga tgggatttct ccaacagaca tctgccaggg gatcctcggg   300
```

-continued

```
gactgctggc tgctggctgc catcggctcc cttaccacct gccccaaact gctataccgc    360
gtggtgccca gaggacagag cttcaagaaa actatgctg gcatcttcca ttttcagatt    420
tggcagtttg acagtgggt gaacgtggtg gtagatgacc ggctgcccac aaagaatgac    480
aagctggtgt tgtgcactc aaccgaacgc agtgagttct ggagtgccct gctggagaag    540
gcgtatgcca agctgagtgg gtcctatgaa gcattgtcag ggggcagtac catggagggc    600
cttgaggact tcacaggagg cgtggcccag agcttccaac tccagaggcc cctcagaac    660
ctgctcaggc tccttaggaa ggccgtggag cgatcctccc tcatgggttg ctccattgaa    720
gtcaccagtg atagtgaact ggaatccatg actgacaaga tgctggtgag agggcacgct    780
tactctgtga ctggccttca ggatgtccac tacagaggca aaatggaaac actgattcgg    840
gtccggaatc cctggggccg gattgagtgg aatggagctt ggagtgacag tgccagggag    900
tgggaagagg tggcctcaga catccagatg cagctgctgc acaagacgga ggacggggag    960
ttctggatgt cctaccaaga tttcctgaac aacttcacgc tcctggagat ctgcaacctc   1020
acgcctgata cactctctgg ggactacaag agctactggc acaccacctt ctacgagggc   1080
agctggcgca gaggcagctc cgcaggggc tgcaggaacc accctggcac gttctggacc   1140
aaccccagt ttaagatctc tcttcctgag ggggatgacc agaggatga cgcagagggc   1200
aatgttgtgg tctgcacctg cctggtggcc ctaatgcaga agaactggcg gcatgcacgg   1260
cagcagggag cccagctgca gaccattggc tttgtcctct acgcggtccc aaaagagttt   1320
cagaacattc aggatgtcca cttgaagaag gaattcttca cgaagtatca ggaccacggc   1380
ttctcagaga tcttcaccaa ctcacggag gtgagcagcc aactccggct gcctccgggg   1440
gaatatatca ttattccctc cacctttgag ccacacagag atgctgactt cctgcttcgg   1500
gtcttcaccg agaagcacag cgagtcatgg gaattggatg aagtcaacta tgctgagcaa   1560
ctccaagagg aaaaggtctc tgaggatgac atggaccagg acttcctaca tttgtttaag   1620
atagtggcag gagagggcaa ggagataggg gtgtatgagc tccagaggct gctcaacagg   1680
atggccatca aattcaaaag cttcaagacc aagggctttg gcctggatgc ttccgctgc   1740
atgatcaacc tcatggataa agatggctct ggcaagctgg ggcttctaga gttcaagatc   1800
ctgtggaaaa aactcaagaa atggatggac atcttcagag agtgtgacca ggaccattca   1860
ggcaccttga actcctatga gatgcgcctg gttattgaga aagcaggcat caagctgaac   1920
aacaaggtaa tgcaggtcct ggtggccagg tatgcagatg atgacctgat catagacttt   1980
gacagcttca tcagctgttt cctgaggcta aagaccatgt tcatggctgc agatgaccat   2040
gtggggatag aggcgctgta g                                              2061
```

<210> SEQ ID NO 8
<211> LENGTH: 686
<212> TYPE: PRT
<213> ORGANISM: homo sapiens

<400> SEQUENCE: 8

```
Met Val Ala His Ile Asn Asn Ser Arg Leu Lys Ala Lys Gly Val Gly
  1               5                  10                  15

Gln His Asp Asn Ala Gln Asn Phe Gly Asn Gln Ser Phe Glu Glu Leu
             20                  25                  30

Arg Ala Ala Cys Leu Arg Lys Gly Glu Leu Phe Glu Asp Pro Leu Phe
         35                  40                  45

Pro Ala Glu Pro Ser Ser Leu Gly Phe Lys Asp Leu Gly Pro Asn Ser
     50                  55                  60
```

-continued

```
Lys Asn Val Gln Asn Ile Ser Trp Gln Arg Pro Lys Asp Ile Ile Asn
 65                  70                  75                  80

Asn Pro Leu Phe Ile Met Asp Gly Ile Ser Pro Thr Asp Ile Cys Gln
                 85                  90                  95

Gly Ile Leu Gly Asp Cys Trp Leu Leu Ala Ala Ile Gly Ser Leu Thr
                100                 105                 110

Thr Cys Pro Lys Leu Leu Tyr Arg Val Val Pro Arg Gly Gln Ser Phe
            115                 120                 125

Lys Lys Asn Tyr Ala Gly Ile Phe His Phe Gln Ile Trp Gln Phe Gly
130                 135                 140

Gln Trp Val Asn Val Val Asp Asp Arg Leu Pro Thr Lys Asn Asp
145                 150                 155                 160

Lys Leu Val Phe Val His Ser Thr Glu Arg Ser Glu Phe Trp Ser Ala
                165                 170                 175

Leu Leu Glu Lys Ala Tyr Ala Lys Leu Ser Gly Ser Tyr Glu Ala Leu
            180                 185                 190

Ser Gly Gly Ser Thr Met Glu Gly Leu Glu Asp Phe Thr Gly Gly Val
        195                 200                 205

Ala Gln Ser Phe Gln Leu Gln Arg Pro Pro Gln Asn Leu Leu Arg Leu
210                 215                 220

Leu Arg Lys Ala Val Glu Arg Ser Ser Leu Met Gly Cys Ser Ile Glu
225                 230                 235                 240

Val Thr Ser Asp Ser Glu Leu Glu Ser Met Thr Asp Lys Met Leu Val
                245                 250                 255

Arg Gly His Ala Tyr Ser Val Thr Gly Leu Gln Asp Val His Tyr Arg
            260                 265                 270

Gly Lys Met Glu Thr Leu Ile Arg Val Arg Asn Pro Trp Gly Arg Ile
        275                 280                 285

Glu Trp Asn Gly Ala Trp Ser Asp Ser Ala Arg Glu Trp Glu Glu Val
        290                 295                 300

Ala Ser Asp Ile Gln Met Gln Leu Leu His Lys Thr Glu Asp Gly Glu
305                 310                 315                 320

Phe Trp Met Ser Tyr Gln Asp Phe Leu Asn Asn Phe Thr Leu Leu Glu
                325                 330                 335

Ile Cys Asn Leu Thr Pro Asp Thr Leu Ser Gly Asp Tyr Lys Ser Tyr
            340                 345                 350

Trp His Thr Thr Phe Tyr Glu Gly Ser Trp Arg Arg Gly Ser Ser Ala
        355                 360                 365

Gly Gly Cys Arg Asn His Pro Gly Thr Phe Trp Thr Asn Pro Gln Phe
370                 375                 380

Lys Ile Ser Leu Pro Glu Gly Asp Asp Pro Glu Asp Asp Ala Glu Gly
385                 390                 395                 400

Asn Val Val Val Cys Thr Cys Leu Val Ala Leu Met Gln Lys Asn Trp
                405                 410                 415

Arg His Ala Arg Gln Gln Gly Ala Gln Leu Gln Thr Ile Gly Phe Val
            420                 425                 430

Leu Tyr Ala Val Pro Lys Glu Phe Gln Asn Ile Gln Asp Val His Leu
        435                 440                 445

Lys Lys Glu Phe Phe Thr Lys Tyr Gln Asp His Gly Phe Ser Glu Ile
        450                 455                 460

Phe Thr Asn Ser Arg Glu Val Ser Gln Leu Arg Leu Pro Pro Gly
465                 470                 475                 480
```

```
Glu Tyr Ile Ile Ile Pro Ser Thr Phe Glu Pro His Arg Asp Ala Asp
                485                 490                 495

Phe Leu Leu Arg Val Phe Thr Glu Lys His Ser Glu Ser Trp Glu Leu
            500                 505                 510

Asp Glu Val Asn Tyr Ala Glu Gln Leu Gln Glu Glu Lys Val Ser Glu
        515                 520                 525

Asp Asp Met Asp Gln Asp Phe Leu His Leu Phe Lys Ile Val Ala Gly
    530                 535                 540

Glu Gly Lys Glu Ile Gly Val Tyr Glu Leu Gln Arg Leu Leu Asn Arg
545                 550                 555                 560

Met Ala Ile Lys Phe Lys Ser Phe Lys Thr Lys Gly Phe Gly Leu Asp
                565                 570                 575

Ala Cys Arg Cys Met Ile Asn Leu Met Asp Lys Asp Gly Ser Gly Lys
            580                 585                 590

Leu Gly Leu Leu Glu Phe Lys Ile Leu Trp Lys Leu Lys Lys Lys Trp
        595                 600                 605

Met Asp Ile Phe Arg Glu Cys Asp Gln Asp His Ser Gly Thr Leu Asn
    610                 615                 620

Ser Tyr Glu Met Arg Leu Val Ile Glu Lys Ala Gly Ile Lys Leu Asn
625                 630                 635                 640

Asn Lys Val Met Gln Val Leu Val Ala Arg Tyr Ala Asp Asp Asp Leu
                645                 650                 655

Ile Ile Asp Phe Asp Ser Phe Ile Ser Cys Phe Leu Arg Leu Lys Thr
            660                 665                 670

Met Phe Met Ala Ala Asp Asp His Val Gly Ile Glu Ala Leu
        675                 680                 685

<210> SEQ ID NO 9
<211> LENGTH: 2806
<212> TYPE: DNA
<213> ORGANISM: homo sapiens

<400> SEQUENCE: 9
caagcaccga gctagccacc agcatgctgt actccccagg gccgagtctt ccggagtcag      60
cagagagcct ggatggatca caggaggata agcctcgggg ctcatgtgcg gagcccactt     120
ttactgatac gggaatggtg gctcacataa acaacagccg gctcaaggcc aagggcgtgg     180
gccagcacga caacgcccag aactttggta accagagctt tgaggagctg cgagcagcct     240
gtctaagaaa gggggagctc ttcgaggacc ccttattccc tgctgaaccc agctcactgg     300
gcttcaagga cctgggcccc aactccaaaa atgtgcagaa catctcctgg cagcggccca     360
aggatatcat aaacaaccct ctattcatca tggatgggat ttctccaaca gacatctgcc     420 agggggatcct cggggactgc tggctgctgg ctgccatcgg ctcccttacc acctgcccca     480
aactgctata ccgcgtggtg cccagaggac agagcttcaa gaaaaactat gctggcatct     540
tccattttca gatttggcag tttggacagt gggtgaacgt ggtggtagat accggctgc     600 ccacaaagaa tgacaagctg gtgtttgtgc actcaaccga acgcagtgag ttctggagtg     660
ccctgctgga gaaggcgtat gccaagctga gtgggtccta tgaagcattg tcaggggca     720 gtaccatgga gggccttgag gacttcacag gaggcgtggc ccagagcttc aactccaga     780 ggccccctca gaacctgctc aggctcctta ggaaggccgt ggagcgatcc tccctcatgg     840
gttgctccat tgaagtcacc agtgatagtg aactggaatc catgactgac aagatgctgg     900
tgagagggca cgcttactct gtgactggcc ttcaggatgt ccactacaga ggcaaaatgg     960
```

-continued

```
aaacactgat tcgggtccgg aatccctggg gccggattga gtggaatgga gcttggagtg    1020
acagtgccag ggagtgggaa gaggtggcct cagacatcca gatgcagctg ctgcacaaga    1080
cggaggacgg ggagttctgg atgtcctacc aagatttcct gaacaacttc acgctcctgg    1140
agatctgcaa cctcacgcct gatacactct ctggggacta caagagctac tggcacacca    1200
ccttctacga gggcagctgg cgcagaggca gctccgcagg gggctgcagg aaccaccctg    1260
gcacgttctg gaccaacccc cagtttaaga tctctcttcc tgaggggat gacccagagg    1320 atgacgcaga gggcaatgtt gtggtctgca cctgcctggt ggccctaatg cagaagaact    1380
ggcggcatgc acggcagcag ggagcccagc tgcagaccat tggctttgtc ctctacgcgg    1440
tcccaaaaga gtttcagaac attcaggatg tccacttgaa gaaggaattc ttcacgaagt    1500
atcaggacca cggcttctca gagatcttca ccaactcacg ggaggtgagc agccaactcc    1560
ggctgcctcc gggggaatat atcattattc cctccacctt tgagccacac agagatgctg    1620
acttcctgct tcgggtcttc accgagaagc acagcgagtc atgggaattg gatgaagtca    1680
actatgctga gcaactccaa gaggaaaagg tctctgagga tgacatggac caggacttcc    1740
tacatttgtt taagatagtg gcaggagagg gcaaggagat aggggtgtat gagctccaga    1800
ggctgctcaa caggatggcc atcaaattca aaagcttcaa gaccaagggc tttggcctgg    1860
atgcttgccg ctgcatgatc aacctcatgg ataaagatgg ctctggcaag ctggggcttc    1920
tagagttcaa gatcctgtgg aaaaaactca agaaatggat ggacatcttc agagagtgtg    1980
accaggacca ttcaggcacc ttgaactcct atgagatgcg cctggttatt gagaaagcag    2040
gcatcaagct gaacaacaag gtaatgcagg tcctggtggc caggtatgca gatgatgacc    2100
tgatcataga ctttgacagc ttcatcagct gtttcctgag gctaaagacc atgttcacat    2160
tctttctaac catggaccccc aagaatactg gccatatttg cttgagcctg aacagtggc    2220 tgcagatgac catgtgggga tagaggcgct gtaggagcct ggtcatctct accagcagca    2280
gcagcagcga ggttctagcc caggagggtg gggtgcttct tgtagccctc agctctccgg    2340
tctctgctga tgaaatgggc tccaggtggc agtgcccggg tcccaggtgc cgtgtttact    2400
gcagcagtgg gacctccgtg cccactcccc cagctcagag gctttctctt ttttccccaa    2460
cccggcttct gatggctggc tttcccccac catcgctctc tcagagtata ttttactaaa    2520
gagtagttga tgcttcccca gggtccccct ggctggggag gccaagaata gggaagggac    2580
ttgtagcccg tttcttaccc tccatgcttg ctgtcctgct cacacctacc tgctgaccac    2640
ccatcctggc acagcctctg ttttcctccc catctgtgga tactattcta ataaatagca    2700
catgccattg gcaaaaaaaa aaaaaaaaaa aaaaaaaaaa aaaaaaaaaa aaaaaaaaaa    2760
aaaaaaaaaa aaaaaaaaaa aaaaaaaaaa aaaaaaaaaa aaaaaa              2806
```

HUMAN CALCIUM DEPENDENT PROTEASES AND POLYNUCLEOTIDES ENCODING THE SAME

The present application claims priority to U.S. Provisional Application Ser. No. 60/152,057, filed Sep. 2, 1999, which is herein incorporated by reference in its entirety.

1. INTRODUCTION

The present invention relates to the discovery, identification, and characterization of novel human polynucleotides encoding proteins that share sequence similarity with human calcium dependent proteases. The invention encompasses the described polynucleotides, host cell expression systems, the encoded proteins, fusion proteins, polypeptides and peptides, antibodies to the encoded proteins and peptides, and genetically engineered animals that either lack or over express the disclosed genes, antagonists and agonists of the proteins, and other compounds that modulate the expression or activity of the proteins encoded by the disclosed genes that can be used for diagnosis, drug screening, clinical trial monitoring and the treatment of physiological disorders.

2. BACKGROUND OF THE INVENTION

Proteases are enzymes that mediate the proteolytic cleavage of polypeptide sequences. In particular, calcium-dependent proteases such as calpains, have been found in virtually every vertebrate cell that has been examined for their presence. The calpain system has at least three well-characterized protein members that are activated in response to changes in calcium concentration. These proteins include at least two calpains that are activated at different concentrations of calcium, and a calpastatin that specifically inhibits the two calpains. Various tissue/species specific cDNAs have been described that are homologous to the calpains. Given the near ubiquitous expression of calpains, they have been implicated in a wide variety of cellular functions including, but not limited to, cell proliferation and differentiation, signal transduction, processes involving interactions between the cell membrane and cytoskeleton, secretion, platelet aggregation, cytokinesis, and disease. Accordingly, calpains represent a key target for the regulation of a variety of biological pathways.

3. SUMMARY OF THE INVENTION

The present invention relates to the discovery, identification, and characterization of nucleotides that encode novel human proteins, and the corresponding amino acid sequences of these proteins. The novel human proteins (NHPs) described for the first time herein share structural similarity with animal calcium-activated proteases, or calpains. As such, the novel genes represent a new class of protease proteins with a range of homologues and orthologs that transcend phyla and a broad range of species.

The novel human nucleic acid sequences described herein, encode proteins/open reading frames (ORFs) of 739, 723, 702, and 686 amino acids in length (see SEQ ID NOS: 2, 4, 6, and 8 respectively).

The invention also encompasses agonists and antagonists of the described NHPs, including small molecules, large molecules, mutant NHPs, or portions thereof that compete with native NHP, peptides, and antibodies, as well as nucleotide sequences that can be used to inhibit the expression of the described NHPs (e.g., antisense and ribozyme molecules, and gene or regulatory sequence replacement constructs) or to enhance the expression of the described NHP genes (e.g., expression constructs that place the described gene under the control of a strong promoter system), and transgenic animals that express a NHP transgene, or "knock-outs" (which can be conditional) that do not express a functional NHP.

Further, the present invention also relates to processes of identifying compounds that modulate, i.e., act as agonists or antagonists, of NHP expression and/or NHP product activity that utilize purified preparations of the described NHPs and/or NHP product, or cells expressing the same. Such compounds can be used as therapeutic agents for the treatment of any of a wide variety of symptoms associated with biological disorders or imbalances.

4. DESCRIPTION OF THE SEQUENCE LISTING AND FIGURES

The Sequence Listing provides the sequences of 4 calpain-like ORFs that encode the described NHP amino acid sequences.

5. DETAILED DESCRIPTION OF THE INVENTION

The NHPS, described for the first time herein, are novel proteins that are expressed in, inter alia, human cell lines, and human prostate and testis, cells. The described sequences were compiled from gene trapped cDNAs and a clone isolated from a human testis cDNA library (Edge Biosystems, Gaithersburg, Md.). The present invention encompasses the nucleotides presented in the Sequence Listing, host cells expressing such nucleotides, the expression products of such nucleotides, and: (a) nucleotides that encode mammalian homologs of the described genes, including the specifically described NHPs, and the NHP products; (b) nucleotides that encode one or more portions of the NHPs that correspond to functional domains, and the polypeptide products specified by such nucleotide sequences, including but not limited to the novel regions of any active domain(s); (c) isolated nucleotides that encode mutant versions, engineered or naturally occurring, of the described NHPs in which all or a part of at least one domain is deleted or altered, and the polypeptide products specified by such nucleotide sequences, including but not limited to soluble proteins and peptides in which all or a portion of the signal sequence in deleted; (d) nucleotides that encode chimeric fusion proteins containing all or a portion of a coding region of an NHP, or one of its domains (e.g., a receptor binding domain, accessory protein/self-association domain, etc.) fused to another peptide or polypeptide; or (e) therapeutic or diagnostic derivatives of the described polynucleotides such as oligonucleotides, antisense polynucleotides, ribozymes, dsRNA, or gene therapy constructs comprising a sequence first disclosed in the Sequence Listing.

As discussed above, the present invention includes: (a) the human DNA sequences presented in the Sequence Listing (and vectors comprising the same) and additionally contemplates any nucleotide sequence encoding a contiguous NHP open reading frame (ORF) that hybridizes to a complement of a DNA sequence presented in the Sequence Listing under highly stringent conditions, e.g., hybridization to filter-bound DNA in 0.5 M NaHPO$_4$, 7% sodium dodecyl sulfate (SDS), 1 mM EDTA at 65° C., and washing in 0.1×SSC/0.1% SDS at 68° C. (Ausubel F. M. et al., eds., 1989, Current Protocols in Molecular Biology, Vol. I, Green Publishing Associates, Inc., and John Wiley & sons, Inc., New York, at p. 2.10.3) and encodes a functionally equivalent gene product. Additionally contemplated are any nucleotide sequences that hybridize to the complement of the DNA sequence that encode and express an amino acid sequence presented in the Sequence Listing under moderately stringent conditions, e.g., washing in 0.2×SSC/0.1% SDS at 42° C. (Ausubel et al., 1989, supra), yet still encode a functionally equivalent NHP product. Functional equivalents of a NHP include naturally occurring NHPs present in other species and mutant NHPs whether naturally occurring or engineered (by site directed mutagenesis, gene shuffling, directed evolution as described in, for example, U.S. Pat. No. 5,837,458). The invention also includes degenerate nucleic acid variants of the disclosed NHP polynucleotide sequences.

The invention also includes nucleic acid molecules, preferably DNA molecules, that hybridize to, and are therefore the complements of, the described NHP gene nucleotide sequences. Such hybridization conditions may be highly stringent or less highly stringent, as described above. In instances where the nucleic acid molecules are deoxyoligonucleotides ("DNA oligos"), such molecules are generally about 16 to about 100 bases long, or about 20 to about 80, or about 34 to about 45 bases long, or any variation or combination of sizes represented therein that incorporate a contiguous region of sequence first disclosed in the Sequence Listing. Such oligonucleotides can be used in conjunction with the polymerase chain reaction (PCR) to screen libraries, isolate clones, and prepare cloning and sequencing templates, etc.

Alternatively, such NHP oligonucleotides can be used as hybridization probes for screening libraries, and assessing gene expression patterns (particularly using. a micro array or high-throughput "chip" format). Additionally, a series of the described NHP oligonucleotide sequences, or the complements thereof, can be used to represent all or a portion of the described NHP sequences. The oligonucleotides, typically between about 16 to about 40 (or any whole number within the stated range) nucleotides in length may partially overlap each other and/or the NHP sequence may be represented using oligonucleotides that do not overlap. Accordingly, the described NHP polynucleotide sequences shall typically comprise at least about two or three distinct oligonucleotide sequences of at least about 18, and preferably about 25, nucleotides in length that are each first disclosed in the described Sequence Listing. Such oligonucleotide sequences may begin at any nucleotide present within a sequence in the Sequence Listing and proceed in either a sense (5'-to-3') orientation vis-a-vis the described sequence or in an antisense orientation.

For oligonucleotide probes, highly stringent conditions may refer, e.g., to washing in 6×SSC/0.05% sodium pyrophosphate at 37° C. (for 14-base oligos), 48° C. (for 17-base oligos), 55° C. (for 20-base oligos), and 60° C. (for 23-base oligos). These nucleic acid molecules may encode or act as NHP gene antisense molecules, useful, for example, in NHP gene regulation (for and/or as antisense primers in amplification reactions of NHP gene nucleic acid sequences). With respect to NHP gene regulation, such techniques can be used to regulate biological functions. Further, such sequences may be used as part of ribozyme and/or triple helix sequences that are also useful for NHP gene regulation.

Inhibitory antisense or double stranded oligonucleotides can additionally comprise at least one modified base moiety which is selected from the group including but not limited to 5-fluorouracil, 5-bromouracil, 5-chlorouracil, 5-iodouracil, hypoxanthine, xantine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3) w, and 2,6-diaminopurine.

The antisense oligonucleotide can also comprise at least one modified sugar moiety selected from the group including but not limited to arabinose, 2-fluoroarabinose, xylulose, and hexose.

In yet another embodiment, the antisense oligonucleotide will comprise at least one modified phosphate backbone selected from the group consisting of a phosphorothioate, a phosphorodithioate, a phosphoramidothioate, a phosphoramidate, a phosphordiamidate, a methylphosphonate, an alkyl phosphotriester, and a formacetal or analog thereof.

In yet another embodiment, the antisense oligonucleotide is an α-anomeric oligonucleotide. An α-anomeric oligonucleotide forms specific double-stranded hybrids with complementary RNA in which, contrary to the usual β-units, the strands run parallel to each other (Gautier et al., 1987, Nucl. Acids Res. 15:6625–6641). The oligonucleotide is a 2'-0-methylribonucleotide (Inoue et al., 1987, Nucl. Acids Res. 15:6131–6148), or a chimeric RNA-DNA analogue (Inoue et al., 1987, FEBS Lett. 215:327–330). Alternatively, double stranded RNA can be used to disrupt the expression and function of a targeted NHP.

Oligonucleotides of the invention can be synthesized by standard methods known in the art, e.g. by use of an automated DNA synthesizer (such as are commercially available from Biosearch, Applied Biosystems, etc.). As examples, phosphorothioate oligonucleotides can be synthesized by the method of Stein et al. (1988, Nucl. Acids Res. 16:3209), and methylphosphonate oligonucleotides can be prepared by use of controlled pore glass polymer supports (Sarin et al., 1988, Proc. Natl. Acad. Sci. U.S.A. 85:7448–7451), etc.

Low stringency conditions are well known to those of skill in the art, and will vary predictably depending on the specific organisms from which the library and the labeled sequences are derived. For guidance regarding such conditions see, for example, Sambrook et al., 1989, Molecular Cloning, A Laboratory Manual (and periodic updates thereof), Cold Springs Harbor Press, N.Y.; and Ausubel et al., 1989, Current Protocols in Molecular Biology, Green Publishing Associates and Wiley Interscience, N.Y.

Alternatively, suitably labeled NHP nucleotide probes can be used to screen a human genomic library using appropriately stringent conditions or by PCR. The identification and characterization of human genomic clones is helpful for identifying polymorphisms (including, but not limited to, nucleotide repeats, microsatellite alleles, single nucleotide polymorphisms, or coding single nucleotide polymorphisms), determining the genomic structure of a given locus/allele, and designing diagnostic tests. For example, sequences derived from regions adjacent to the intron/exon boundaries of the human gene can be used to design primers for use in amplification assays to detect mutations within the exons, introns, splice sites (e.g., splice acceptor and/or donor sites), etc., that can be used in diagnostics and pharmacogenomics.

Further, a NHP gene homolog can be isolated from nucleic acid from an organism of interest by performing PCR using two degenerate or "wobble" oligonucleotide primer pools designed on the basis of amino acid sequences within the NHP products disclosed herein. The template for the reaction may be total RNA, mRNA, and/or cDNA obtained by reverse transcription of mRNA prepared from, for example, human or non-human cell lines or tissue, such as prostate, testes, rectum, colon, or adrenal gland, known or suspected to express an allele of a NHP gene.

The PCR product can be subcloned and sequenced to ensure that the amplified sequences represent the sequence of the desired NHP gene. The PCR fragment can then be used to isolate a full length cDNA clone by a variety of methods. For example, the amplified fragment can be labeled and used to screen a cDNA library, such as a bacteriophage cDNA library. Alternatively, the labeled fragment can be used to isolate genomic clones via the screening of a genomic library.

PCR technology can also be used to isolate full length cDNA sequences. For example, RNA can be isolated, following standard procedures, from an appropriate cellular or tissue source (i.e., one known, or suspected, to express a NHP gene, such as, for example, testis tissue). A reverse transcription (RT) reaction can be performed on the RNA using an oligonucleotide primer specific for the most 5' end of the amplified fragment for the priming of first strand synthesis. The resulting RNA/DNA hybrid may then be "tailed" using a standard terminal transferase reaction, the hybrid may be digested with RNase H, and second strand synthesis may then be primed with a complementary primer. Thus, CDNA sequences upstream of the amplified fragment can be isolated. For a review of cloning strategies that can be used, see e.g., Sambrook et al., 1989, supra.

A CDNA encoding a mutant NHP gene can be isolated, for example, by using PCR. In this case, the first cDNA strand may be synthesized by hybridizing an oligo-dT oligonucleotide to mRNA isolated from tissue known or suspected to be expressed in an individual putatively carrying a mutant NHP allele, and by extending the new strand with reverse transcriptase. The second strand of the cDNA is then synthesized using an oligonucleotide that hybridizes specifically to the 5' end of the normal gene. Using these two primers, the product is then amplified via PCR, optionally cloned into a suitable vector, and subjected to DNA sequence analysis through methods well known to those of skill in the art. By comparing the DNA sequence of the mutant NHP allele to that of a corresponding normal NHP allele, the mutation(s) responsible for the loss or alteration of function of the mutant NHP gene product can be ascertained.

Alternatively, a genomic library can be constructed using DNA obtained from an individual suspected of or known to carry a mutant NHP allele (e.g., a person manifesting a NHP-associated phenotype such as, for example, obesity, high blood pressure, etc.), or a cDNA library can be constructed using RNA from a tissue known, or suspected, to express a mutant NHP allele. A normal NHP gene, or any suitable fragment thereof, can then be labeled and used as a probe to identify the corresponding mutant NHP allele in such libraries. Clones containing mutant NHP gene sequences can then be purified and subjected to sequence analysis according to methods well known to those skilled in the art.

Additionally, an expression library can be constructed utilizing cDNA synthesized from, for example, RNA isolated from a tissue known, or suspected, to express a mutant NHP allele in an individual suspected of or known to carry such a mutant allele. In this manner, gene products made by the putatively mutant tissue may be expressed and screened using standard antibody screening techniques in conjunction with antibodies raised against a normal NHP product, as described below. (For screening techniques, see, for example, Harlow, E. and Lane, eds., 1988, "Antibodies: A Laboratory Manual", Cold Spring Harbor Press, Cold Spring Harbor.)

Additionally, screening can be accomplished by screening with labeled NHP fusion proteins, such as, for example, AP-NHP or NHP-AP fusion proteins. In cases where a NHP mutation results in an expressed gene product with altered function (e.g., as a result of a missense or a frameshift mutation), polyclonal antibodies to a NHP are likely to cross-react with a corresponding mutant NHP gene product. Library clones detected via their reaction with such labeled antibodies can be purified and subjected to sequence analysis according to methods well known in the art.

The invention also encompasses (a) DNA vectors that contain any of the foregoing NHP coding sequences and/or their complements (i.e., antisense); (b) DNA expression vectors that contain any of the foregoing NHP coding sequences operatively associated with a regulatory element that directs the expression of the coding sequences (for example, baculo virus as described in U.S. Pat. No. 5,869, 336 herein incorporated by reference); (c) genetically engineered host cells that contain any of the foregoing NHP coding sequences operatively associated with a regulatory element that directs the expression of the coding sequences in the host cell; and (d) genetically engineered host cells that express an endogenous NHP gene under the control of an exogenously introduced regulatory element (i.e., gene activation). As used herein, regulatory elements include but are not limited to inducible and non-inducible promoters, enhancers, operators and other elements known to those skilled in the art that drive and regulate expression. Such regulatory elements include but are not limited to the cytomegalovirus (hCMV) immediate early gene, regulatable, viral (particularly retroviral LTR promoters) the early or late promoters of SV40 adenovirus, the lac system, the trp system, the TAC system, the TRC system, the major operator and promoter regions of phage lambda, the control regions of fd coat protein, the promoter for 3-phosphoglycerate kinase (PGK), the promoters of acid phosphatase, and the promoters of the yeast α-mating factors.

The present invention also encompasses antibodies and anti-idiotypic antibodies (including Fab fragments), antagonists and agonists of the NHP, as well as compounds or nucleotide constructs that inhibit expression of a NHP gene (transcription factor inhibitors, antisense and ribozyme molecules, or gene or regulatory sequence replacement constructs), or promote the expression of a NHP (e.g., expression constructs in which NHP coding sequences are operatively associated with expression control elements such as promoters, promoter/enhancers, etc.).

The NHPs or NHP peptides, NHP fusion proteins, NHP nucleotide sequences, antibodies, antagonists and agonists can be useful for the detection of mutant NHPs or inappropriately expressed NHPs for the diagnosis of disease. The NHP proteins or peptides, NHP fusion proteins, NHP nucleotide sequences, host cell expression systems, antibodies, antagonists, agonists and genetically engineered cells and animals can be used for screening for drugs (or high throughput screening of combinatorial libraries) effective in the treatment of the symptomatic or phenotypic manifestations of perturbing the normal function of NHP in the body. The use of engineered host cells and/or animals may offer an advantage in that such systems allow not only for the identification of compounds that bind to the endogenous receptor for an NHP, but can also identify compounds that trigger NHP-mediated signal transduction.

Finally, the NHP products can be used as therapeutics. For example, soluble derivatives such as NHP peptides/domains corresponding the NHPs, NHP fusion protein products (especially NHP-Ig fusion proteins, i.e., fusions of a NHP, or a domain of a NHP, to an IgFc), NHP antibodies and anti-idiotypic antibodies (including Fab fragments), antagonists or agonists (including compounds that modulate signal transduction which may act on downstream targets in a NHP-mediated signal transduction pathway) can be used to directly treat diseases or disorders. For instance, the administration of an effective amount of soluble NHP, or a NHP-IgFc fusion protein or an anti-idiotypic antibody (or its Fab) that mimics the NHP could activate or effectively antagonize the endogenous NHP receptor. Nucleotide constructs encoding such NHP products can be used to genetically engineer host cells to express such products in vivo; these genetically engineered cells function as "bioreactors" in the body delivering a continuous supply of a NHP, a NHP peptide, or a NHP fusion protein to the body. Nucleotide constructs encoding functional NHPs, mutant NHPs, as well as antisense and ribozyme molecules can also be used in "gene therapy" approaches for the modulation of NHP expression. Thus, the invention also encompasses pharmaceutical formulations and methods for treating biological disorders.

A knockout ES cell clone has been produced in a murine gene encoding an ortholog of the disclosed NHPs.

Various aspects of the invention are described in greater detail in the subsections below.

5.1 THE NHP SEQUENCES

The cDNA sequences (SEQ ID NOS: 1, 3, 5, 7, and 9) and the corresponding deduced amino acid sequences (SEQ ID NOS: 2, 4, 6, and 8) of the described NHPs are presented in the Sequence Listing. The NHP genes were obtained from a human testis cDNA library using probes and/or primers generated from human gene trapped sequence tags. Expression analysis has provided evidence that the described NHPs can be expressed, for example, in human testis, prostate, and gene trapped human cells. In addition to the human calpain gene, the described NHPs share significant similarity to a variety of proteases from mice, pigs, chickens, and rats.

The described open reading frames can also contain several polymorphisms including an A to G transition corresponding to base 1474 (changing a K to an E), a C to T transition corresponding to base 1669 (changing a Q to a stop codon that truncates the ORF), and a T to A transversion corresponding to base 1673 (changing a L to an H) of SEQ ID NOS: 1 and 3.

5.2 NHPS AND NHP POLYPEPTIDES

NHPs, polypeptides, peptide fragments, mutated, truncated, or deleted forms of the NHPs, and/or NHP fusion proteins can be prepared for a variety of uses. These uses include but are not limited to the generation of antibodies, as reagents in diagnostic assays, to identify other cellular gene products related to a NHP, as reagents in screening assays for compounds that can be used as pharmaceutical reagents useful in the therapeutic treatment of mental, biological, or medical disorders and disease.

The Sequence Listing discloses the amino acid sequences encoded by the described NHP genes. The NHPs have initiator methionines in DNA sequence contexts consistent with a translation initiation site. The sequence data presented herein indicate that alternatively spliced forms of the NHPs exist (which may or may not be tissue specific).

The NHP amino acid sequences of the invention include the nucleotide and amino acid sequences presented in the Sequence Listing as well as analogues and derivatives thereof. Further, corresponding NHP homologues from other species are encompassed by the invention. In fact, any NHP protein encoded by the NHP nucleotide sequences described above, are within the scope of the invention, as are any novel polynucleotide sequences encoding all or any novel portion of an amino acid sequence presented in the Sequence Listing. The degenerate nature of the genetic code is well known, and, accordingly, each amino acid presented in the Sequence Listing, is generically representative of the well known nucleic acid "triplet" codon, or in many cases codons, that can encode the amino acid. As such, as contemplated herein, the amino acid sequences presented in the Sequence Listing, when taken together with the genetic code (see, for example, Table 4-1 at page 109 of "Molecular Cell Biology", 1986, J. Darnell et al. eds., Scientific American Books, New York, N.Y., herein incorporated by reference) are generically representative of all the various permutations and combinations of nucleic acid sequences that can encode such amino acid sequences.

The invention also encompasses proteins that are functionally equivalent to the NHPs encoded by the presently described nucleotide sequences as judged by any of a number of criteria, including, but not limited to, the ability to bind and cleave a substrate of a NHP, or the ability to effect an identical or complementary downstream signal transduction pathway, or a change in cellular metabolism (e.g., proteolytic activity, ion flux, tyrosine phosphorylation, etc.). Such functionally equivalent NHP roteins include, but are not limited to, additions or substitutions of amino acid residues within the amino acid sequence encoded by the NHP nucleotide sequences described above, but which result in a silent change, thus producing a functionally equivalent gene product. Amino acid substitutions may be made on the basis of similarity in polarity, charge, solubility, hydrophobicity, hydrophilicity, and/or the amphipathic nature of the residues involved. For example, nonpolar (hydrophobic) amino acids include alanine, leucine, isoleucine, valine, proline, phenylalanine, tryptophan, and methionine; polar neutral amino acids include glycine, serine, threonine, cysteine, tyrosine, asparagine, and glutamine; positively charged (basic) amino acids include arginine, lysine, and histidine; and negatively charged (acidic) amino acids include aspartic acid and glutamic acid.

A variety of host-expression vector systems can be used to express the NHP nucleotide sequences of the invention. Where the NHP peptide or polypeptide is a soluble derivative of, for example, a membrane protein (e.g., NHP peptides derived from an extracellular domain (ECD) of a NHP, or truncated or deleted NHPs in which a transmembrane (TM) and/or cytoplasmic domain (CD) have been deleted, etc.) the peptide or polypeptide can be recovered from the culture, i.e., from the host cell in cases where the NHP peptide or polypeptide is not secreted, or from the culture media in cases where the NHP peptide or polypeptide is secreted by the cells. However, such expression systems also encompass engineered host cells that express a NHP, or functional equivalent, in situ, i.e., anchored in the cell membrane. Purification or enrichment of a NHP from such expression systems can be accomplished using appropriate detergents and lipid micelles and methods well known to those skilled in the art. Alternatively, such engineered host cells themselves may be used in situations where it is important not only to retain the structural and functional characteristics of the NHP, but to assess biological activity, e.g., in drug screening assays.

The expression systems that may be used for purposes of the invention include but are not limited to microorganisms such as bacteria (e.g., *E. coli, B. subtilis*) transformed with recombinant bacteriophage DNA, plasmid DNA or cosmid DNA expression vectors containing NHP nucleotide sequences; yeast (e.g., *Saccharomyces, Pichia*) transformed with recombinant yeast expression vectors containing NHP nucleotide sequences; insect cell systems infected with recombinant virus expression vectors (e.g., baculovirus) containing NHP sequences; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing NHP nucleotide sequences; or mammalian cell systems (e.g., COS, CHO, BHK, 293, 3T3) harboring recombinant expression constructs containing promoters derived from the genome of mammalian cells (e.g., metallothionein promoter) or from mammalian viruses (e.g., the adenovirus late promoter; the vaccinia virus 7.5K promoter).

In bacterial systems, a number of expression vectors may be advantageously selected depending upon the use intended for the NHP product being expressed. For example, when a large quantity of such a protein is to be produced for the generation of pharmaceutical compositions of or containing NHP, or for raising antibodies to a NHP, vectors that direct the expression of high levels of fusion protein products that are readily purified may be desirable. Such vectors include, but are not limited to, the *E. coli* expression vector pUR278 (Ruther et al., 1983, EMBO J. 2:1791), in which a NHP coding sequence may be ligated individually into the vector in frame with the lacZ coding region so that a fusion protein is produced; pIN vectors (Inouye & Inouye, 1985, Nucleic Acids Res. 13:3101–3109; Van Heeke & Schuster, 1989, J. Biol. Chem. 264:5503–5509); and the like. pGEX vectors may also be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. The PGEX vectors are designed to include thrombin or factor Xa protease cleavage sites so that the cloned target gene product can be released from the GST moiety.

In an insect system, *Autographa californica* nuclear polyhidrosis virus (AcNPV) is used as a vector to express foreign genes. The virus grows in *Spodoptera frugiperda* cells. A NHP gene coding sequence may be cloned individually into non-essential regions (for example the polyhedrin gene) of the virus and placed under control of an AcNPV promoter (for example the polyhedrin promoter). Successful insertion of NHP gene coding sequence will result in inactivation of the polyhedrin gene and production of non-occluded recombinant virus (i.e., virus lacking the proteinaceous coat coded for by the polyhedrin gene). These recombinant viruses are then used to infect *Spodoptera frugiperda* cells in which the inserted gene is expressed (e.g., see Smith et al., 1983, J. Virol. 46:584; Smith, U.S. Pat. No. 4,215,051).

In mammalian host cells, a number of viral-based expression systems may be utilized. In cases where an adenovirus is used as an expression vector, the NHP nucleotide sequence of interest may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing a NHP product in infected hosts (e.g., See Logan & Shenk, 1984, Proc. Natl. Acad. Sci. USA 81:3655–3659). Specific initiation signals may also be required for efficient translation of inserted NHP nucleotide sequences. These signals include the ATG initiation codon and adjacent sequences. In cases where an entire NHP gene or cDNA, including its own initiation codon and adjacent sequences, is inserted into the appropriate expression vector, no additional translational control signals may be needed. However, in cases where only a portion of a NHP coding sequence is inserted, exogenous translational control signals, including, perhaps, the ATG initiation codon, must be provided. Furthermore, the initiation codon must be in phase with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. (See Bittner et al., 1987, Methods in Enzymol. 153:516–544).

In addition, a host cell strain may be chosen that modulates the expression of the inserted sequences, or modifies and processes the gene product in the specific fashion desired. Such modifications (e.g., glycosylation) and processing (e.g., cleavage) of protein products may be important for the function of the protein. Different host cells have characteristic and specific mechanisms for the post-translational processing and modification of proteins and gene products. Appropriate cell lines or host systems can be chosen to ensure the correct modification and processing of the foreign protein expressed. To this end, eukaryotic host cells which possess the cellular machinery for proper processing of the primary transcript, glycosylation, and phosphorylation of the gene product may be used. Such mammalian host cells include, but are not limited to, CHO, VERO, BHK, HeLa, COS, MDCK, 293, 3T3, WI38, and in particular, human cell lines.

For long-term, high-yield production of recombinant proteins, stable expression is preferred. For example, cell lines which stably express the NHP sequences described above may be engineered. Rather than using expression vectors which contain viral origins of replication, host cells can be transformed with DNA controlled by appropriate expression control elements (e.g., promoter, enhancer sequences, transcription terminators, polyadenylation sites, etc.), and a selectable marker. Following the introduction of the foreign DNA, engineered cells may be allowed to grow for 1–2 days in an enriched media, and then are switched to a selective media. The selectable marker in the. recombinant plasmid confers resistance to the selection and allows cells to stably integrate the plasmid into their chromosomes and grow to form foci which in turn can be cloned and expanded into cell lines. This method may advantageously be used to engineer cell lines which express the NHP product. Such engineered cell lines may be particularly useful in screening and evaluation of compounds that affect the endogenous activity of the NHP product.

A number of selection systems may be used, including but not limited to the herpes simplex virus thymidine kinase (Wigler, et al., 1977, Cell 11:223), hypoxanthine-guanine phosphoribosyltransferase (Szybalska & Szybalski, 1962, Proc. Natl. Acad. Sci. USA 48:2026), and adenine phosphoribosyltransferase (Lowy, et al., 1980, Cell 22:817) genes can be employed in tk⁻, hgprt⁻ or aprt⁻ cells, respectively. Also, antimetabolite resistance can be used as the basis of selection for the following genes: dhfr, which confers resistance to methotrexate (Wigler, et al., 1980, Natl. Acad. Sci. USA 77:3567; O'Hare, et al., 1981, Proc. Natl. Acad. Sci. USA 78:1527); gpt, which confers resistance to mycophenolic acid (Mulligan & Berg, 1981, Proc. Natl. Acad. Sci. USA 78:2072); neo, which confers resistance to the aminoglycoside G-418 (Colberre-Garapin, et al., 1981, J. Mol. Biol. 150:1); and hygro, which confers resistance to hygromycin (Santerre, et al., 1984, Gene 30:147).

Alternatively, any fusion protein may be readily purified by utilizing an antibody specific for the fusion protein being expressed. For example, a system described by Janknecht et al. allows for the ready purification of non-denatured fusion proteins expressed in human cell lines (Janknecht, et al., 1991, Proc. Natl. Acad. Sci. USA 88:8972–8976). In this system, the gene of interest is subcloned into a vaccinia recombination plasmid such that the gene's open reading frame is translationally fused to an amino-terminal tag consisting of six histidine residues. Extracts from cells infected with recombinant vaccinia virus are loaded onto $Ni^{2+}$-nitriloacetic acid-agarose columns and histidine-tagged proteins are selectively eluted with imidazole-containing buffers.

5.3 ANTIBODIES TO NHP PRODUCTS

Antibodies that specifically recognize one or more epitopes of a NHP, or epitopes of conserved variants of a NHP, or peptide fragments of a NHP are also encompassed by the invention. Such antibodies include but are not limited to polyclonal antibodies, monoclonal antibodies (mAbs), humanized or chimeric antibodies, single chain antibodies, Fab fragments, F(ab')₂ fragments, fragments produced by a Fab expression library, anti-idiotypic (anti-Id) antibodies, and epitope-binding fragments of any of the above.

The antibodies of the invention may be used, for example, in the detection of NHP in a biological sample and may, therefore, be utilized as part of a diagnostic or prognostic technique whereby patients may be tested for abnormal amounts of NHP. Such antibodies may also be utilized in conjunction with, for example, compound screening schemes, as described, below, in Section 5.5, for the evaluation of the effect of test compounds on expression and/or activity of a NHP gene product. Additionally, such antibodies can be used in conjunction gene therapy to, for example, evaluate the normal and/or engineered NHP-expressing cells prior to their introduction into the patient. Such antibodies may additionally be used as a method for the inhibition of abnormal NHP activity. Thus, such antibodies may, therefore, be utilized as part of treatment methods.

For the production of antibodies, various host animals may be immunized by injection with the NHP, an NHP peptide (e.g., one corresponding to a functional domain of an NHP), truncated NHP polypeptides (NHP in which one or more domains have been deleted), functional equivalents of the NHP or mutated variant of the NHP. Such host animals may include but are not limited to pigs, rabbits, mice, goats, and rats, to name but a few. Various adjuvants may be used to increase the immunological response, depending on the host species, including but not limited to Freund's adjuvant (complete and incomplete), mineral salts such as aluminum hydroxide or aluminum phosphate, surface active substances such as lysolecithin, pluronic polyols, polyanions, peptides, oil emulsions and potentially useful human adjuvants such as BCG (bacille Calmette-Guerin) and *Corynebacterium parvum*. Alternatively, the immune response could be enhanced by combination with molecules such as keyhole limpet hemocyanin, tetanus toxoid, diptheria toxoid, ovaolbumin, cholera toxoid or fragments thereof. Polyclonal antibodies are heterogeneous populations of antibody molecules derived from the sera of the immunized animals.

Monoclonal antibodies, which are homogeneous populations of antibodies to a particular antigen, may be obtained by any technique which provides for the production of antibody molecules by continuous cell lines in culture. These include, but are not limited to, the hybridoma technique of Kohler and Milstein, (1975, Nature 256:495–497; and U.S. Pat. No. 4,376,110), the human B-cell hybridoma technique (Kosbor et al., 1983, Immunology Today 4:72; Cole et al., 1983, Proc. Natl. Acad. Sci. USA 80:2026–2030), and the EBV-hybridoma technique (Cole et al., 1985, Monoclonal Antibodies And Cancer Therapy, Alan R. Liss, Inc., pp. 77–96). Such antibodies may be of any immunoglobulin class including IgG, IgM, IgE, IgA, IgD and any subclass thereof. The hybridoma producing the mAb of this invention may be cultivated in vitro or in vivo. Production of high titers of mAbs in vivo makes this the presently preferred method of production.

In addition, techniques developed for the production of "chimeric antibodies" (Morrison et al., 1984, Proc. Natl. Acad. Sci., 81:6851–6855; Neuberger et al., 1984, Nature, 312:604–608; Takeda et al., 1985, Nature, 314:452–454) by splicing the genes from a mouse antibody molecule of appropriate antigen specificity together with genes from a human antibody molecule of appropriate biological activity can be used. A chimeric antibody is a molecule in which different portions are derived from different animal species, such as those having a variable region derived from a murine mAb and a human immunoglobulin constant region. Such technologies are described in US Pat. Nos. 6,075,181 and 5,877,397 and their respective disclosures which are herein incorporated by reference in their entirety.

Alternatively, techniques described for the production of single chain antibodies (U.S. Pat. No. 4,946,778; Bird, 1988, Science 242:423–426; Huston et al., 1988, Proc. Natl. Acad. Sci. USA 85:5879–5883; and Ward et al., 1989, Nature 334:544–546) can be adapted to produce single chain antibodies against NHP gene products. Single chain antibodies are formed by linking the heavy and light chain fragments of the Fv region via an amino acid bridge, resulting in a single chain polypeptide.

Antibody fragments which recognize specific epitopes may be generated by known techniques. For example, such fragments include, but are not limited to: the F(ab')₂ fragments which can be produced by pepsin digestion of the antibody molecule and the Fab fragments which can be generated by reducing the disulfide bridges of the F(ab')₂ fragments. Alternatively, Fab expression libraries may be constructed (Huse et al., 1989, Science, 246:1275–1281) to allow rapid and easy identification of monoclonal Fab fragments with the desired specificity.

Antibodies to a NHP can, in turn, be utilized to generate anti-idiotype antibodies that "mimic" a given NHP, using techniques well known to those skilled in the art. (See, e.g., Greenspan & Bona, 1993, FASEB J 7(5):437–444; and Nissinoff, 1991, J. Immunol. 147(8):2429–2438). For example antibodies which bind to a NHP domain and competitively inhibit the binding of NHP to its cognate receptor can be used to generate anti-idiotypes that "mimic" the NHP and, therefore, bind and activate or neutralize a receptor. Such anti-idiotypic antibodies or fragments of such anti-idiotypes can be used in therapeutic regimens involving a NHP signaling pathway.

The present invention is not to be limited in scope by the specific embodiments described herein, which are intended as single illustrations of individual aspects of the invention, and functionally equivalent methods and components are within the scope of the invention. Indeed, various modifications of the invention, in addition to those shown and described herein will become apparent to those skilled in the art from the foregoing description. Such modifications are intended to fall within the scope of the appended claims.

What is claimed is:

1. An isolated nucleic acid molecule comprising the nucleotide sequence of SEQ ID NO: 1.

2. An isolated nucleic acid molecule comprising a nucleotide sequence that encodes the amino acid sequence shown in SEQ ID NO:2.

* * * * *